(12) United States Patent
Kanesaka

(10) Patent No.: US 6,283,990 B1
(45) Date of Patent: Sep. 4, 2001

(54) COMBINATION OF BALLOON AND STENT WITH SPECIFIC SIZES

(76) Inventor: Nozomu Kanesaka, 81 Greenwoods Rd., Old Tappan, NJ (US) 07675

( * ) Notice: Subject to any disclaimer, the term of this patent is extended or adjusted under 35 U.S.C. 154(b) by 0 days.

(21) Appl. No.: 09/569,238

(22) Filed: May 11, 2000

(51) Int. Cl.$^7$ .......................................... A61F 2/03
(52) U.S. Cl. .............................................. 623/1.11
(58) Field of Search ................... 623/1.11, 1.12, 623/1.13, 1.16, 1.15, 1.2, 1.3; 606/191, 195, 198, 194, 192

(56) References Cited

U.S. PATENT DOCUMENTS 6,056,776 * 5/2000 Lau et al. ............................. 623/1.16

* cited by examiner

Primary Examiner—Henry J. Recla
Assistant Examiner—Kevin Truong
(74) Attorney, Agent, or Firm—Kanesaka & Takeuchi

(57) ABSTRACT

A balloon having a predetermined maximum expandable size is combined with a stent having a predetermined maximum expandable size, which is equal to the maximum expandable size of the balloon. The stent is formed of a plurality of rows of cylindrical strut sections situated side by side in a longitudinal direction, and a plurality of connecting members for connecting two rows of the struts adjacent to each other. The strut section includes struts, and bending portions located at ends of the struts. A strut angle is defined by the strut and a line parallel to a central axis of the stent and extending through the bending portion. The strut angle is at least 75 degrees and less than 90 degrees when the stent is fully expanded. Thus, the stent fully expanded by the balloon is not easily collapsed.

7 Claims, 3 Drawing Sheets

COMBINATION OF BALLOON AND STENT WITH SPECIFIC SIZES

BACKGROUND OF THE INVENTION AND RELATED ART STATEMENT

The present invention relates to a combination of a balloon and a stent with specific sizes, wherein the stent is opened substantially to the maximum opening size by the balloon with substantially the same maximum opening size to provide an effective retaining or supporting ability to the stent in a vessel.

The most of the current stents on the market including coronary and peripheral stents are designed to have struts, and elbows or bending portions, wherein the struts in one strut section are bent at the elbows and arranged to have a zigzag shape as a whole. Some of the elbows in one strut section are connected to the elbows in the adjacent strut section. When the stent is in a closed condition, the struts are situated substantially parallel to the stent axis. As the stent begins to open by inflating a balloon on which the stent is mounted, an angle between two struts connected with each other through the elbow in between becomes wider.

In general, all the currently available stents are designed to cover all sizes by one or two stents in a coronary market. The range of the diameter when it is opened is between 2.5 mm and 4.0 mm.

There are two factors in determining the size of the stent in the open condition. One is the size of the balloon to be used, and the other is an inflating pressure applied to the balloon. For example, if a balloon with 3.0 mm in diameter is used, the stent will open to 3.0 mm in diameter. If a higher pressure is applied, the balloon may expand slightly more, so that the stent may become 3.2 mm in diameter.

The stents are generally sold in a package, so-called pre-mount stents. In the pre-mount stents, the stents are already mounted on various balloons, which respectively have various diameters, such as 2.5 mm, 3.0 mm, 3.5 mm, and 4.0 mm. Although the balloons are different in the pre-mount stents to equally open the stents in the various diameters, a common stent which opens to various diameters is mostly used for those balloons having different diameters.

More specifically, as shown in FIG. 4, a conventional stent 101 used for all types of the balloons has a cylindrical shape and a diameter D101 in a closed condition, and mounted on a balloon 102 of a balloon catheter 103, known in the art, as shown in FIG. 5.

After the stent is delivered to a specific position by the balloon catheter 103, an inflating pressure is applied inside the balloon 102 so that the balloon 102 is inflated to have an opening diameter D102 as shown in FIG. 6. Accordingly, the stent 101 mounted on the balloon 102 is opened by the balloon 102 to have the opening diameter D102. For example, the diameter D102 is 2.5 mm. In the open stent shown in FIG. 6, an angle formed by a strut 104 and an axis A parallel to a central axis of the stent 101 is 40 degrees.

When the stent 101 is mounted on a balloon 102' of a balloon catheter 103' in which an opening diameter of the balloon 102' is larger than D102, the stent 101 is further opened to have a diameter D103 which is larger than the diameter D102. For example, the diameter D103 is 3 mm, and an angle formed by the strut 104 and the axis A of the stent 101 is 50 degrees as shown in FIG. 7.

As described above, since the stent 101 having the same size, such as the diameter D101, in the closed condition is used for the various balloons 102, 102' having various diameters D102, D103 in the opened condition, the inflating pressures applied inside the balloons 102, 102' are increased and the angles between the strut 104 and the axis of the stent 101 becomes larger as the diameter of the balloon becomes larger.

Namely, if the stent is opened to have a diameter close to the maximum opening diameter, the strut angles, as mentioned above, become obtuse. Thus, it requires more pressure to open the stent to have the maximum diameter. This is very desirable to the stent since it takes more pressure to close or collapse the stent. In other words, when the stent is opened to the maximum diameter, the stent has a high withstanding force against collapsing.

Thus, in the examples shown in FIGS. 6 and 7, the stent 101 shown in FIG. 7 has the withstanding force against collapsing stronger than that shown in FIG. 6. In this sense, although the same stent 101 is used, the ability for supporting is different according to the diameters of the balloons used in the blood vessel.

On the other hand, there is a prior art publication indicating that the struts are bent perpendicular to the stent axis, which is most desirable in supporting the blood vessel. Although this statement is true, it is almost impossible to expand the struts perpendicular to the axis of the stent by the balloon because it requires too high inflating pressure by the balloon. The relationship of the angle of the strut relative to the pressure applied to the strut is show below, wherein the angle is measured as in FIGS. 6 and 7.

| Angle(degrees) | Pressure(ATM) |
| --- | --- |
| 15 | 1.00 |
| 30 | 2.15 |
| 45 | 3.73 |
| 60 | 6.46 |
| 75 | 13.93 |
| 80 | 21.17 |
| 85 | 42.66 |

As shown above, it requires about 42 ATM to open the strut at 85 degrees. This is practically impossible to open the strut by the balloon. The balloon now available in the market can provide 12 to 20 ATM.

The present invention has been made in view of the above, and an object of the invention is to provide a combination of a specific size balloon and a specific size stent, wherein each stent is designed to open to the specific one size only to prevent collapsing of the stent after enlargement.

Another object of the invention is to provide a combination of the balloon and stent as stated above, wherein the stent is enlarged to the maximum size as designed to be used for a long time without trouble.

Further objects and advantages of the invention will be apparent from the following description of the invention.

SUMMARY OF THE INVENTION

In the present invention, a balloon having a predetermined maximum expandable size is combined with an expandable stent to be expanded by the balloon. The stent has a predetermined maximum expandable size equal to the maximum expandable size of the balloon.

The stent is formed of a plurality of rows of cylindrical strut sections situated side by side in a longitudinal direction to form the stent, and a plurality of connecting members for connecting two rows of the struts adjacent to each other. Each strut section in one row is formed of struts, and bending portions located at respective ends of the struts. A strut angle is defined by the strut and a line parallel to a central axis of the stent and extending through the bending portion. In the invention, the strut angle is at least 75 degrees, i.e. equal to or more than 75 degrees, and less than 90 degrees when the stent is fully expanded. Practically, the strut angle is between 75 and 80 degrees. When the stent is fully expanded by the balloon, the stent is not easily collapsed with less recoil. Thus, the stent can be used in a blood vessel or other portion for a long time without causing trouble.

In this respect, if the stent is expanded less than 75 degrees, the stent may be collapsed in a long usage or when a large collapsible force is applied to the stent for a long time. Also, the stent may recoil a lot. Thus, the strut angle is required at least 75 degrees.

In the invention, the balloon for the specific maximum expandable size is combined with the stent for the specific maximum expandable size. If the balloon for the large size is used for enlarging the small size stent, the stent may not be equally expanded at the maximum expanded condition. In order to fully and equally expand the stent, the balloon for the specific maximum expandable size must be used for the stent with the same specific maximum expandable size.

Preferably, the struts in the strut section are arranged side by side around the axis of the stent to form a zig-zag pattern. The struts in the strut section may be arranged substantially parallel to each other when the stent is mounted on the balloon before expansion.

DETAILED DESCRIPTION OF PREFERRED EMBODIMENTS

Embodiments of the invention will be explained with reference to the accompanying drawings.

Figure 1:
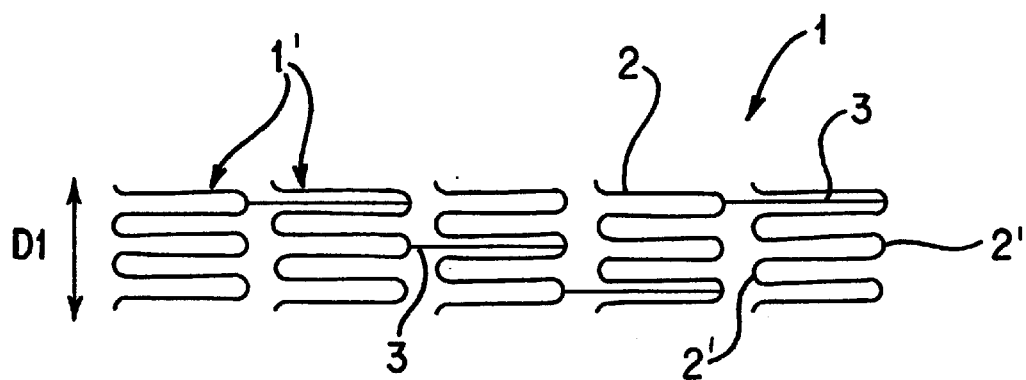
FIG. 1 is a schematic side view of a stent used in the present invention, wherein a stent is in a collapsed or closed condition.
Figure 2:
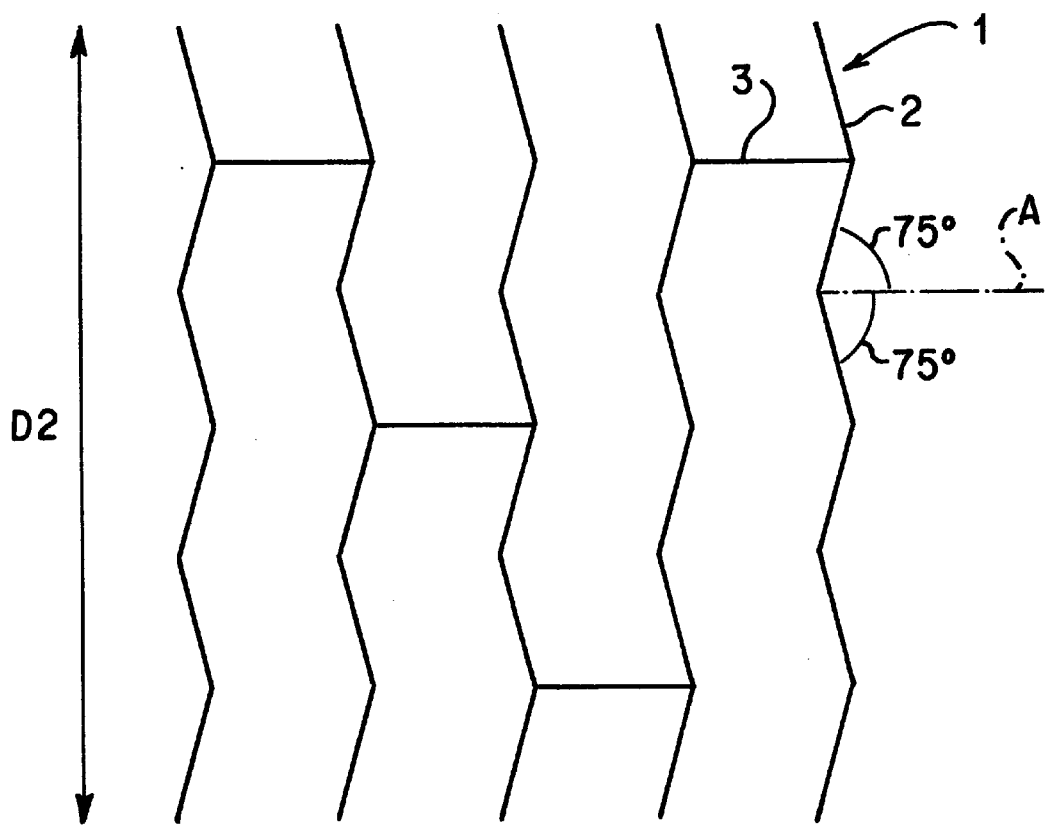
FIG. 2 is a schematic side view of the stent used in the present invention, wherein the stent is in an open or enlarged condition.

FIG. 1 is side view of a collapsed or closed condition of a stent 1, and FIG. 2 shows a side view of an enlarged condition thereof expanded by a balloon. As shown in FIG. 1, the stent 1 has a cylindrical shape, and is formed of a plurality of strut sections 1' situated side by side along a longitudinal direction of the stent 1. Each strut section 1' is formed of struts 2, and bending portions 2' at the ends of the struts 2 to form a zig-zag shape. One or a plurality of elbows or connecting portions 3 connects the bending portion 2' in one strut section to that of the adjacent strut section 1'. In the closed condition, the stent 1 has a diameter D1 as shown in FIG. 1.

When the stent 1 is opened by a balloon, as shown in FIG. 2, the stent 1 has a diameter D2 larger than D1, and an angle formed by the strut 2 and a line A passing through the bending portion 2' and parallel to a central axis of the stent 1 is set to be 75 degrees or more, which is a desirable to withstand a radial force against collapsing.

Figure 3:
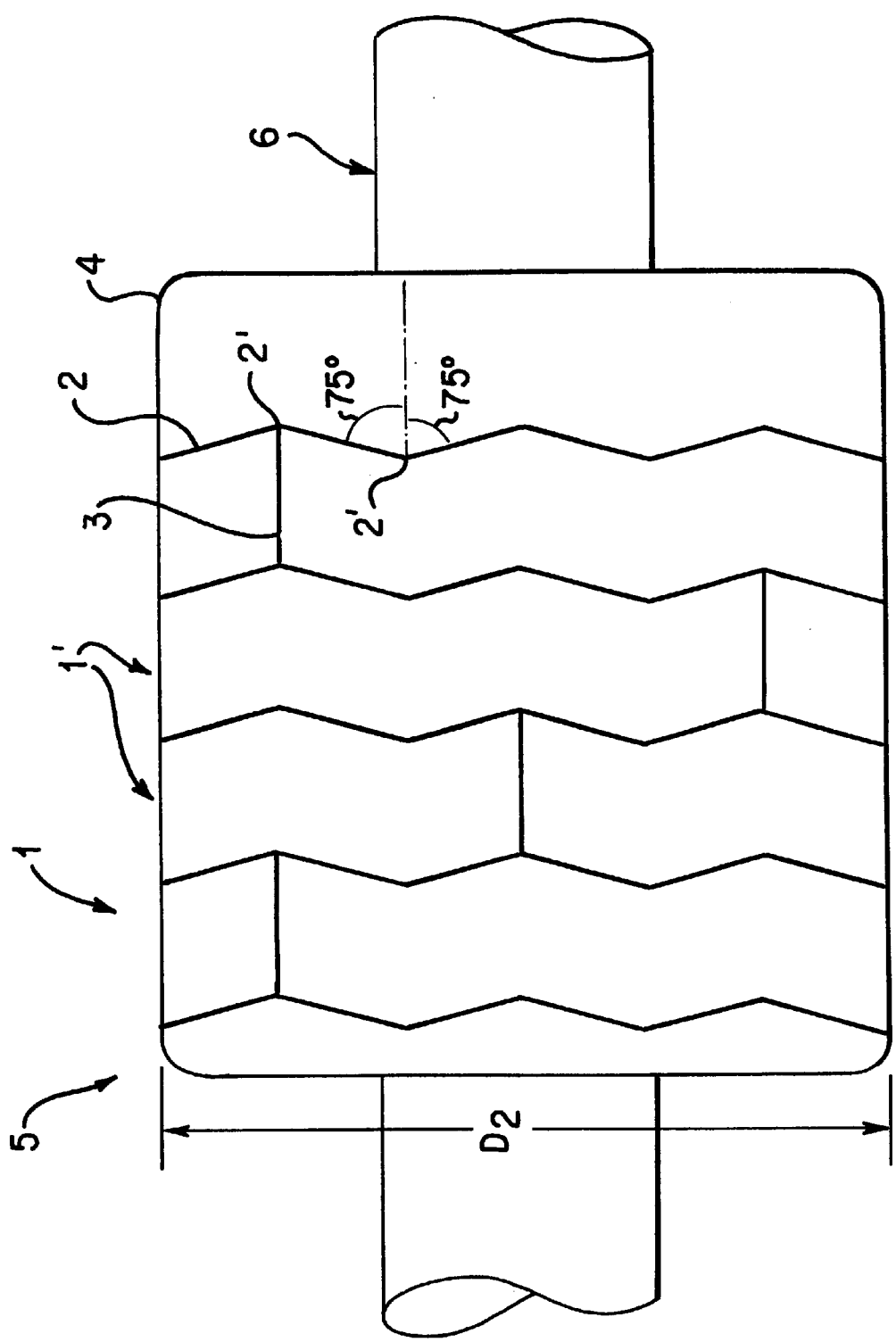
FIG. 3 is an enlarged, schematic side view of the stent shown in FIG. 2 in a condition that the stent is mounted on a balloon of a balloon catheter.
Figure 4:
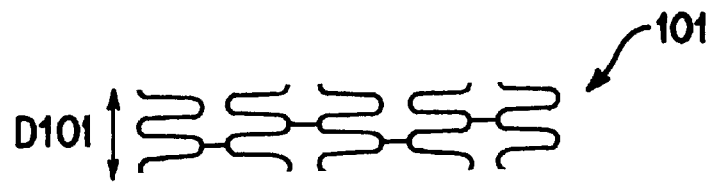
FIG. 4 is a schematic side view of a conventional stent in a closed condition.
Figure 5:
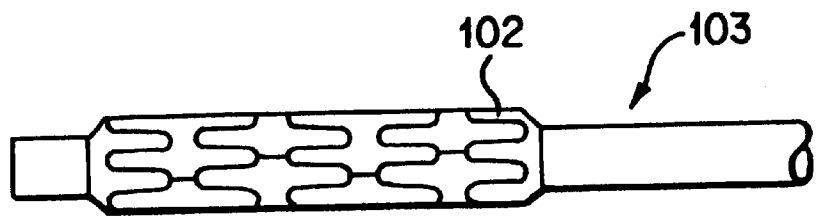
FIG. 5 is a schematic side view of the conventional stent in the condition that the stent as shown in FIG. 4 is mounted on a balloon of a balloon catheter.
Figure 6:
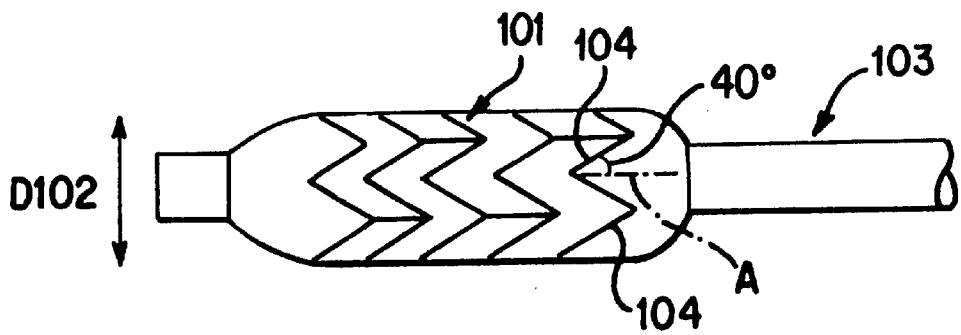
FIG. 6 is a schematic side view of the conventional stent of FIG. 4 expanded to one specific size by the balloon catheter.
Figure 7:
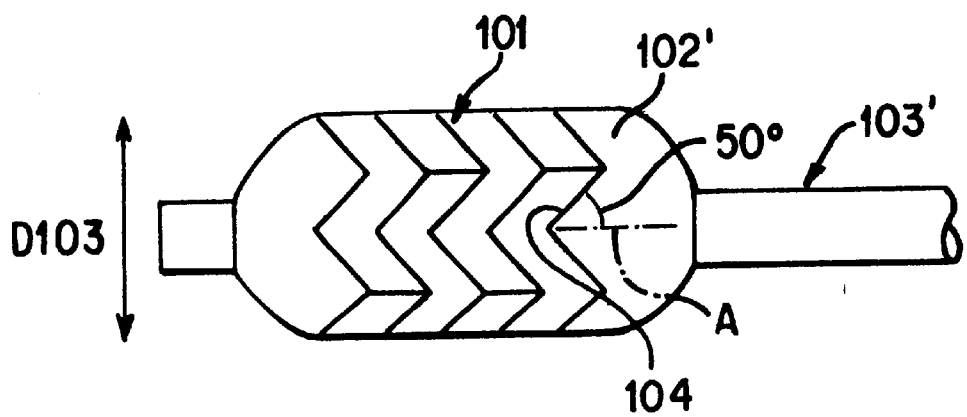
FIG. 7 is a schematic side view of the conventional stent similar to FIG. 6 expanded to a large specific size by a large balloon catheter.

The diameter D2 of the stent 1 in the open condition is set in advance, which corresponds to a diameter of an inflated balloon on which the stent 1 is mounted to be delivered in a blood vessel. Namely, as in the conventional balloon, the stent 1 is mounted on a balloon 4 attached at a distal end portion 5 of a balloon catheter 6, partly shown in FIG. 3, and is opened by the balloon 4 by a pressure applied inside the balloon 4 through an inflating passageway, not shown, formed in the balloon catheter 6. The enlarged diameter of the balloon 4 corresponds to the diameter D2 of the open stent 1.

In the present invention, the stent 1 is made specific to the size of the balloon 4 used for delivering the stent 1. Thus, the stent 1 is designed to open to the specific one size only, and a strut angle, that is, the angle formed by the strut 2 and the line A of the stent 1, is set to be at least 75 degrees or higher, but less than 90 degrees when the stent 1 is opened. Preferably, the strut angle is between 75 and 80 degrees. The stent 1 is maximally opened for the particular size of the balloon 4, so that the stent opened to the specific strut angle withstands relatively large collapsing force applied thereto.

For example, the stent 1 is designed to have an opening diameter D2 of 2.5 mm with the strut angle of 75 degrees, which is opened by the balloon 4 having a 2.5 mm opening diameter. In this case, a circumference of the stent 1 is 7.85 mm. The lengths of the respective strut 2 are set to be 0.81, 0.68 and 0.58 mm when ten, twelve and fourteen struts 2 are used to form the stent 1. The relations of the diameters, the lengths of the circumferences, the lengths of the struts in case of strut angle of 75 degrees are shown below (units are mm):

| | | Strut length | | |
|---|---|---|---|---|
| Diameter | Circumference | 10 struts | 12 struts | 14 struts |
| 2.5 | 7.85 | 0.81 | 0.68 | 0.58 |
| 3.0 | 9.42 | 0.98 | 0.81 | 0.70 |
| 3.5 | 10.99 | 1.14 | 0.95 | 0.81 |
| 4.0 | 12.56 | 1.30 | 1.08 | 0.93 |

In the examples of the aforementioned stents 1 which have the different sizes and configurations corresponding to the different opening diameters of the balloons 4, the strut angle when the stent 1 is opened remains the same, that is, 75 degrees or more, so that the stent 1 has the constant withstanding force against collapsing even if the diameters of the balloons are different.

Thus, as long as the strut angle when the stent is opened remains 75 degrees or more, but less than 90 degrees, the arrangement or shapes of the struts as well as the elbows can be modified.

According to the present invention, the stent having the specific opening size is combined with a balloon with the specific opening size. Thus, when the stent is opened, the strut angle defined by the strut and the line extending through the bending portion and parallel to the stent axis is 75 degrees or more, which is desirable to withstand collapsing of the stent.

The stents of the invention may have different diameters, circumferences, and the length of the struts so as to correspond to the various diameters of the balloons while the strut angle remains the same and is more than 75 degrees. Thus, the respective stents for the various balloons can have the uniform withstanding force against collapsing.

While the invention has been explained with reference to the specific embodiments of the invention, the explanation is illustrative and the invention is limited only by the appended claims.

What is claimed is:

1. A combination comprising a balloon and an expandable stent to be expanded by the balloon, said balloon having a predetermined maximum expandable size, and said stent having a predetermined maximum expandable size equal to said maximum expandable size of the balloon when expanded by the balloon, and comprising:

a plurality of rows of cylindrical strut sections situated side by side in a longitudinal direction to form the stent, each of said strut sections in one row having struts, and bending portions located at ends of the struts to form a strut angle defined by the strut and a line parallel to a central axis of the stent and extending through the bending portion, said strut angle being at least 75 degrees and less than 90 degrees when the stent is fully expanded by the maximum expandable size of the balloon so that the stent fully expanded by the balloon is not easily collapsed; and a plurality of connecting members for connecting two rows of the cylindrical strut sections adjacent to each other.

2. A combination according to claim 1, wherein said struts in the strut section are arranged side by side around the central axis of the stent to form a zig-zag pattern.

3. A combination according to claim 2, wherein said struts in the strut sections are arranged substantially parallel to each other before expansion.

4. A combination according to claim 2, wherein when an expanded diameter of the stent is 2.5 mm, a length of each of the struts is in a range of 0.58 mm to 0.81 mm.

5. A combination according to claim 2, wherein when an expanded diameter of the stent is 3.0 mm, a length of each of the struts is in a range of 0.70 mm to 0.98 mm.

6. A combination according to claim 2, wherein when an expanded diameter is 3.5 mm, a length of each of the struts is in a range of 0.81 mm to 1.14 mm.

7. A combination according to claim 2, wherein when an expanded diameter is 4.0 mm, a length of each of the struts is in a range of 0.93 mm to 1.30 mm.

* * * * *